United States Patent
Karapasha et al.

(10) Patent No.: US 6,652,477 B2
(45) Date of Patent: Nov. 25, 2003

(54) TAMPON APPLICATOR WITH PETALS

(75) Inventors: Nancy Karapasha, Cincinnati, OH (US); Clare Jessamyn Dibble, Cincinnati, OH (US); Jennifer Ann Kraynak Orriss, West Chester, OH (US); Michael Sean Farrell, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/923,201

(22) Filed: Aug. 6, 2001

(65) Prior Publication Data

US 2003/0028138 A1 Feb. 6, 2003

(51) Int. Cl.[7] ................................................ A61F 13/20
(52) U.S. Cl. .......................................... 604/14; 264/339
(58) Field of Search ........................ 604/11–18, 57–60, 604/311; 264/296, 299, 339

(56) References Cited

U.S. PATENT DOCUMENTS

| | | | | |
|---|---|---|---|---|
| 3,358,686 A | * | 12/1967 | Asaka | |
| 4,412,833 A | * | 11/1983 | Wiegner et al. | |
| 4,573,964 A | * | 3/1986 | Huffman | |
| 5,087,239 A | * | 2/1992 | Beastall et al. | |
| 5,389,067 A | * | 2/1995 | Rejai | |
| 5,501,063 A | * | 3/1996 | Tews et al. | |
| 5,693,009 A | | 12/1997 | Fox et al. | |
| 5,746,710 A | * | 5/1998 | Nielsen et al. | |
| 5,766,145 A | | 6/1998 | Fox et al. | |
| 5,782,793 A | | 7/1998 | Nielsen et al. | |
| 5,792,096 A | | 8/1998 | Rentmeester et al. | |

* cited by examiner

*Primary Examiner*—Dennis Ruhl
(74) *Attorney, Agent, or Firm*—Bridget D. Ammons; Kevin C. Johnson; Theodore P. Cummings

(57) ABSTRACT

This invention relates to a tampon applicator, having a specific insertion tip structure with overlapping petals, connected to a tube. The petals are preferably curved such that one edge of a petal has an angle with the top edge of the tube of 40° to 60°. The petals are at least partially closed over the tampon and easily openable in use, which provides an improved, safer and more hygienic insertion of the tampon into the body.

14 Claims, 5 Drawing Sheets

TAMPON APPLICATOR WITH PETALS

FIELD OF THE INVENTION

This invention relates to a tampon applicator, having a specific insertion tip structure with petals, which is closed over the tampon and opens in use, which provides an improved, safer and more hygienic insertion of the tampon into the body.

BACKGROUND OF THE INVENTION

A wide variety of absorbent catamenial tampons and applicators have been described in the art. The applicators are typically devices to facilitate the insertion of the tampon in the body. They are typically made from cardboard or plastic. Current, commercially available applicators include for example those, which comprise two tubes, telescoped in one another, whereof one tube can move inside the other tube, to push the tampon therein forward and thereby expelling it into the vagina. The applicator is then removed from the vagina, leaving the tampon behind. Another common applicator-tampon arrangement is in the form of a plunger with an inserter tube. These type of applicators often have a closed insertion tip with petals, which are integral with the remaining part of the applicator, and which open under application of pressure by the tampon (when the user pushes the tampon) to expel the tampon in the body. Also, because the petals cover the tampon, the tampon remains hygienic prior to use, at least some user find an applicator with a closed insertion tip more hygienic than an open-ended applicator.

However, these petals may also create problems for some users. The petals are perceived as sharp and stiff and that it is possible that they can hurt the body during insertion, in particular when a petal is slightly bend out of plane, prior to insertion. For example, a petal may open prior to use and then, insertion of the applicator may cause harm to the body, e.g. may scratch the vagina. Also, the petals do not always open easily, which means that the user has to use a substantive amount of pressure to expel the tampon past the petals, into the body. This causes also the insertion tip to pinch the user and thereby cause discomfort for the user.

One proposed solution to provide smoother insertion is described in U.S. Pat. No. 5,766,145, suggesting to provide an applicator made of a double layer of material, which has integral therewith a number of petals, which are thinner than the remaining part of the applicator and made of only a single layer. The petals are more flexible and said to provide a smoother insertion. This document also describes that it is important that the expulsion force (e.g. the force to expel a tampon, applied from the inside on the tampon, applicator and petals thereof) should be quite low. The thin, single layered petals are said to provide an acceptable expulsion force. However, because the petals described in this document are thin, there is a high risk that they open prematurely, which makes the applicator less hygienic and which still creates a risk that an opened petal can scratch the body during insertion.

The inventors thus found that there is a need for a tampon-applicator which on one hand has a low expulsion force (to expel tampon through the petals), and which on the other hand has petals that can resist high external forces (e.g. prior to the application of the expulsion force from the inside) to avoid a petal to open prematurely. The inventors have now found an alternative way to provide a solution to these conflicting problems.

They found as solution to these problems a tampon applicator with petals, which are constructed such that they have an overlapping area with one another. The overlapping petals keep one another in place prior to use and prior to the application of the expulsion force from the inside, without the need of making each individual petal very force-resistant, stiff or hard. They can thus even be made of very thinner materials (which may be even more comfortable to insert in the body) without the risk that one or more petals is opened by an external force, at the wrong moment. Meanwhile, because each individual, overlapping petal does not have to be very force resistant in order to avoid opening of that petal, the total petal construction is very easily opened when a force pushes from the inside on all petals, e.g. when the tampon is being expelled through all petals. Thus an applicator is obtained which requires only a very low expulsion force to expel a tampon through the petals, whilst having a reduced risk that one or more individual petals open before insertion, i.e. whilst not requiring a high external force to open a single petal. Thus the applicator of the invention has a smoother, safer and more comfortable insertion, whilst still providing a hygienic covering of the tampon prior to use.

They also found that by providing petals which have a specific angle with the edge of the applicator tube from which they extend, petals can be obtained which do not have a sharp point top, as the petals of the prior art applicators have, but which have more rounded top edges; this again provide a smoother and safer insertion, because no sharp pointy tops can pinch the body during insertion. This angle also aids the reduction of the expulsion force and this angle improves the resistance of an individual petal to prematurely open.

They furthermore found that it is beneficial if there is an opening at the top of the applicator, such that the petals almost converge at the top but leave an about circular opening. They found that the shortest dimension through the geometrical center point of this opening can be an important factor too, to control the force to open one single petal of the insertion tip construction of the invention.

SUMMARY OF THE INVENTION

The present invention relates to an applicator for a tampon, capable of receiving a tampon, having a tube with a first end portion and a second end portion, the first end portion having an end portion edge, which is connected to or integral with an insertion tip, said insertion tip extending from said end portion edge and having at least 2 petals, which each have a first edge and a second edge, extending from said end portion edge, characterised in that of each petal, the first edge is positioned on top of one directly neighbouring petal and the second edge is positioned under another directly neighbouring petal, to form for each petal a region of overlap, with a neighbouring petal.

These regions of overlap are generally in a regular manner, such as having the same pattern of overlap, same size of overlap. Preferably of each petal, the first edge is positioned on top of one directly neighbouring petal and the second edge is positioned under another directly neighbouring petal, to form for each petal a region of overlap. The overlap between a first petal, and the directly neighbouring, second petal is preferably at least 1% of the surface area of the second petal preferably at least 3% or even at least 8% or even at least 10% or even at least 15% or even at least 20% of the surface area of the second petal, typically up to 70% or even 50% or even 35% of the surface are of the second petal.

The first edge is preferably a leading edge which has an angle with the end portion edge $A_t$ of between 20° and 80°, preferably 40° to 60°, and the second edge is a trailing edge which has an angle with the end portion edge $A_t$ of 180°—$A_t$; or the second edge is a leading edge which has an angle with the end portion edge $A_t$ of between 20° and 80°, preferably 40° to 60°, and the first edge is a trailing edge which has an angle with the end portion edge $A_t$ of 180°—$A_t$. The edges are preferably curved in the plane of the petals, as can be seen in the drawings herein, and preferably, the edges of each petal converge towards the highest point of the insertion tip in curving manner, e.g. such that in the top of the insertion tip there are no sharp points of converging petal edges, as also can be seen in the drawings herein.

The invention also provides an applicator for a tampon, capable of receiving a tampon, having a first end portion and a second end portion, the first end portion having an end portion edge, which is connected to or integral with an insertion tip, said insertion tip extending from said end portion edge and having at least 2 petals, which each have a first edge and a second edge, extending from said end portion edge, and whereby the first edge and the second edge converge or optionally are connected with a third edge, at the top region of the insertion tip, and whereby there is an opening in the top region of the insertion tip, characterised that the force to open a petal is at least 50 gram-force and preferably up to 400 g-force and the shortest dimension through the geometrical centre point of the opening (herein after referred to as 'shortest dimension) is less than 10 mm or even less than 5 mm, and preferably at least 2 mm.

The expulsion force to expel the tampon from the applicator is typically less than 500 g-force, preferably less than 400 g-force or even less than 325 g-force and whereby the force to open a single petal is more than 50 g-force, preferably more than 90 g-force.

BRIEF DESCRIPTION OF THE FIGURES

FIG. 2b shows a schematic drawing of a series of 6 petals as can be used to form the applicator of FIGS. 1a, b and 2a;

DETAILED DESCRIPTION OF THE INVENTION

Figure 1A:
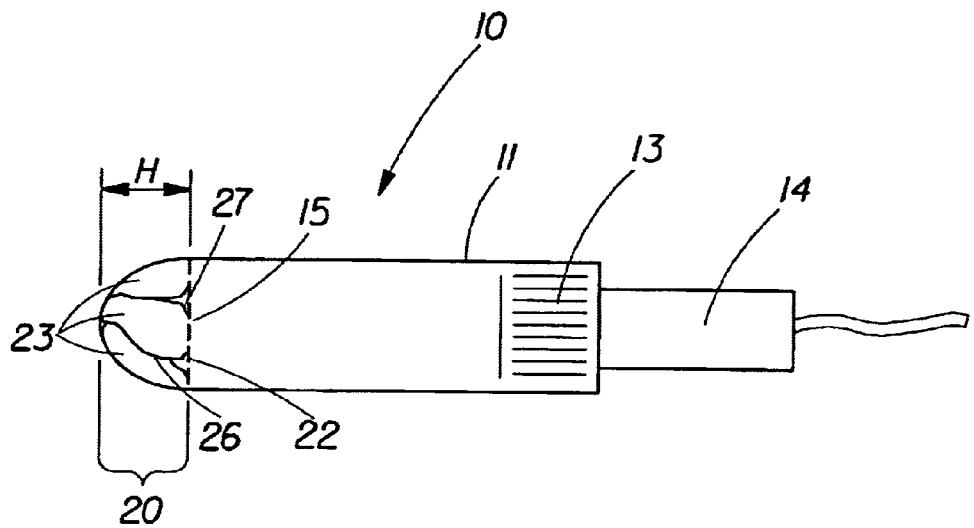
FIG. 1a shows a side view of a preferred applicator of the invention having 6 curved petals.

The invention relates to an applicator, which contains at least a tube and an insertion tip with at least 2 petals, connected to said tube or integral with the tube. The applicator is such that it can hold a tampon or part thereof in its interior, and thus, the applicator is typically hollow. Thus, the tampon or a part thereof is covered or enclosed by the applicator.

The applicator may have any shape, including straight, non-linear or curved shapes. The applicator tube is preferably substantially cylindrical, having an endless sidewall.

The tube has a first end portion and a second end portion, the first end portion having an end portion edge, which is connected to or integral with an insertion tip with the petals.

The insertion tip may have any size and dimension. Preferably, the insertion tip is parabola-shaped, preferably rounded or dome-shaped, preferably being hemispherically shaped. The insertion tip preferably has a tip opening, typically at or around about the top, highest point or highest side of the insertion tip.

The petals may have any size and shape. In the first embodiment of the invention they have an area of overlap, as described herein after in detail with reference to the figures. The applicator may be made of plastic, paper, cardboard or other suitable material. Preferred other materials include degradable or compostable thermoplastic materials, preferably water dispersible or water-soluble materials, preferably biodegradable materials, as known in the art. The applicator may comprise more additional components, for example a second tube or a plunger or pusher.

Thus, the applicator may be a combination of a so-called plunger and an applicator unit with the insertion tip and (cylindrical) tube, capable of holding the tampon, or part thereof. Such an applicator also typically has gripping means at the trailing bottom end (versus insertion top end) of the unit or the plunger. Then, in a common design, the insertion of the tampon is accomplished by grasping and holding a gripping means, then pushing the rear end of the plunger towards the gripping means. The force used during the pushing forces the plunger or applicator unit to contact the tampon and then forces the tampon against the petals, whereby the petals are opened and the tampon can travel past the petals into the body. This is then the expulsion force required to expel the tampon through the petals. This is herein also referred to as internal force onto the petals or force from the inside on the petals, since it acts from inside of the applicator onto the inside of the insertion tip and petals thereof. The external force on the petals as used herein, refers to the force applied from the outside of the applicator on one (or more) petal, such as to open said petal, e.g. by peeling one petal away from the surface of the insertion tip.

One other preferred applicator type is a so-called telescoping arrangement, whereby two units or more can move in or around one another, like a telescope, one of which will contain a tube and the insertion tip with the petals, and one of which may have gripping means. The units are preferably semi rigid, like cardboard or rigid like plastic. They are typically cylindrical shaped, typically like (at least partially) hollow tubes. A first applicator unit (tube with insertion tip with petals) may then contain or hold part of or the entire tampon, and a second applicator unit (tube) can move inside the first applicator unit, and engage the tampon, thereby pushing the tampon out of the first applicator unit, through the petals, as described above.

Preferred may be that the applicator is flushable through the toilet. Preferred may be that the applicator comprises one or more applicator units, which are produced from a spiral-wound paperboard construction, and which are preferably coated on the exterior with a coating material, such as wax. Preferred applicators, insertion tips and petals are further described below with reference to the figures.

As used herein the term "tampon" refers to any type of absorbent structure, which is inserted into the vaginal canal or other body cavities for the absorption of fluid there from, or for the delivery of actives materials, such as medicaments, or moisture. Preferred herein are catamenial tampons, for insertion in the vagina. As used herein the terms 'vagina' includes the vaginal cavity or vaginal interior and refers to the internal genitalia of the human female in the pudendal region of the body.

Typically, tampons are constructed from an absorbent material, which has been compressed in any or all of the width direction, the radial direction, and the axial direction, in order to provide a tampon, which is of a size and stability to allow insertion within the vagina or other body cavity. The tampon is preferably in a so-called 'self-sustaining' form, e.g. it will tend to retain its general shape and size, before use. This self-sustaining form need not persist during actual use of the tampon. The tampons herein are typically fluid expanding, e.g. the tampon will expand (or un-compress) upon contact with fluid such as bodily fluids.

The tampon has a top portion, having a topside or top (point) and a bottom side or point, both typically positioned at or forming the ends of the longitudinal axis of the tampon. The top portion of the tampon is typically the portion, which is positioned under the petals, thus typically the part from the top edge of the tube of the applicator to the top of the inserter tip. Because the inserter tip has preferably an opening at the top, part of the op portion of the tampon may be visible through this opening. The tampon has an insertion end and a withdrawal end, whereby the insertion end contains or is typically said top portion, whilst the withdrawal end contains said bottom side.

The tampon may be straight or non linear in shape, such as curved along the longitudinal axis. If the tampon is straight, the length of tampon is the longest distance between the top portion and bottom side and this is generally parallel to or even equal to the longitudinal axis of the tampon.

If the tampon is curved, the length is the longest absolute length between the topside and bottom side, thus measured along the curved line (longitudinal axis), which typically curves in an equal manner as the tampon.

The tampon has a width, which may vary in different portions of the tampon. If the tampon is straight, the transverse axis of the tampon is preferably perpendicular to the longitudinal axis and then the tampon width is typically perpendicular to the length. Often, the tampon is typically cylindrical, having preferably an endless sidewall or endless longitudinal side, preferably with a flat bottom side and with a rounded or dome-shaped top portion; then, the width of the tampon corresponds to the largest cylindrical cross-section diameter, and the length corresponds to the longest distance between the bottom side and the top of the rounded portion.

The tampon may be a non-layered, uniform structure, or it may be a laminar structure comprised of integral or discrete layers, or the tampon may have a folded structure, or it may be rolled, or any other of the structures which are known in the art. Generally, the tampon herein has to have a certain minimal rigidity, to facilitate the expulsion through the film cap.

The tampon may be constructed from a wide variety of liquid-absorbing materials commonly used in absorbent articles such as rayon, cotton, or comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these. Preferred absorbent materials comprise cotton, rayon (including tri-lobal and conventional rayon fibers, and needle punched rayon), folded tissues, woven materials, nonwoven webs, synthetic and/or natural fibers. The tampon and any component thereof may comprise a single material or a combination of materials. Acceptable types of rayon include GALAXY Rayon (a tri-lobed rayon structure) available as 6140 Rayon from Acordis Fibers Ltd., of Hollywall, England and SARILLE L rayon (a round fiber rayon), also available from Acordis Fibers Ltd. Suitable cotton material includes, long fiber cotton, short fiber cotton, cotton linters, T-fiber cotton, card strips, and comber cotton.

Additionally, superabsorbent materials, such as superabsorbent polymers or absorbent gelling materials may be incorporated into the tampon.

The absorbent material may be surrounded with a liquid permeable material, if desired. Such materials may comprise rayon, cotton, bicomponent fibers, or other suitable natural or synthetic fibers known in the art. Rayon, polyethylene, polypropylene and blends of these are particularly suited for use as cover material.

It is desirable that the tampons of the present invention are made in the absorbency ranges, which are currently required, by the United States Food and Drug Administration and corresponding agencies of many other governments, which regulate tampon absorbency.

The tampon typically contains a withdrawal cord or string, which is generally attached to at least the withdrawal bottom side of the tampon. This may be any type of withdrawal cord known in the art, for example a generally braided (or twisted) withdrawal cord. A conventional type of withdrawal cord (in terms of thickness, material composition, etc.) may be periodically braided with a thicker slub of absorbent fibrous material, which acts as an absorbing member, to form a structure to be connected to the remaining of the tampon. In such an embodiment, the portion of the cord, which will act as the withdrawal cord, may be treated to make it non-absorbent or even hydrophobic. It may also be a withdrawal cord as described in commonly assigned and co-pending U.S. application Ser. No. 09/309,467, filed on May 10, 1999 in the name of Taylor et al. The tampon may contain any additional functional ingredients, such as antimicrobial agents, lubricants, antioxidants etc, as known in the art.

Preferred tampons, sold as 'Regular', comprise a mass of absorbent material which has been compressed into a generally cylindrical, self-sustaining form, with a diameter of less that about 15 mm. The resulting tampon has an absorbent capacity as measured by the standard syngyna test of between about 6 to about 9 grams. The tampon is then fluid expanding and preferably has an expanded width upon fluid absorption of at least about 20 mm. Preferably, the difference between the absorbent material diameter and the tampon expanded width is at least about 6 mm, or even at least about 10 mm. Preferred tampons herein, sold as a "Super" absorbency tampon, compressed into a generally cylindrical, self-sustaining form, may have a diameter of less that about 19 mm. The resulting tampon has an absorbent capacity as measured by the standard syngyna test of between about 9 to about 12 grams. The tampon is then fluid expanding and preferably has an expanded width upon fluid absorption of at least about 24 mm. Preferably, the difference between the absorbent material diameter and the 'Super' tampon expanded width is at least about 8 mm, or even at least about 12 mm. Preferably, the mass of absorbent material is subjected to microwave radiation during formation of the finished tampon.

It may be preferred that the tampon may comprise a chevron shaped (laminar) pad. This pad has a width and a length wherein the width is greater than the length. The pad may comprise at least three layers of absorbent material, including an uppermost layer, a lowermost layer, and at least one intermediate layer positioned between said uppermost layer and said lowermost layer. Each of the uppermost layer and the lowermost layer is comprised primarily of rayon, and the at least one intermediate layer is comprised primarily of cotton.

The applicator of the invention will now be described in more detail with reference to the figures. The figures also serve to exemplify preferred executions of the applicator of the invention. The figures are however not meant to limit the invention by any way.

FIG. 1a shows a side view of an applicator 10 of the invention. The applicator 10 has a tube 11. This tube 11 may have as preferred component a gripping means 13, which facilitates the grip and hold by the user of the tube 11. The applicator 10 also has an insertion tip 20. The applicator also may have a plunger 14 or a telescoping second tube, which can be pushed inside the tube 11 to engage with the tampon, which is inside the tube 11 and not visible, to push the tampon out of the tube 11 through the insertion tip 20. The tube 11 is cylindrical and straight but of course other shapes are envisaged herein. The insertion tip 20 may be a separate component, connected to the tube 11, or it may be integral with the tube 1, as is shown in FIG. 1a.

The tube has a first end portion and a second end portion. The first end portion has an end portion edge 15, which is the line of the connecting area of the tip 20 and the tube 11, if these are separate components, connected to one another; or if these are integral with one another, the edge 15 is the imaginary line through the (imaginary) bottom lines 22 of the petals 23 of the insertion tip 20.

The insertion tip 20 has at least 2 petals 23, up to a maximum of any number of petals. Preferred may be that the insertion tip 20 has 3, 4, 5 or 6 petals. Preferred may be 3 or 4 petals, to further increase the force required to open a single petal while maintaining an acceptable expulsion force. The petals 23 lie typically on the top portion of the tampon and cover all or part of the tampon top portion.

Figure 1B:
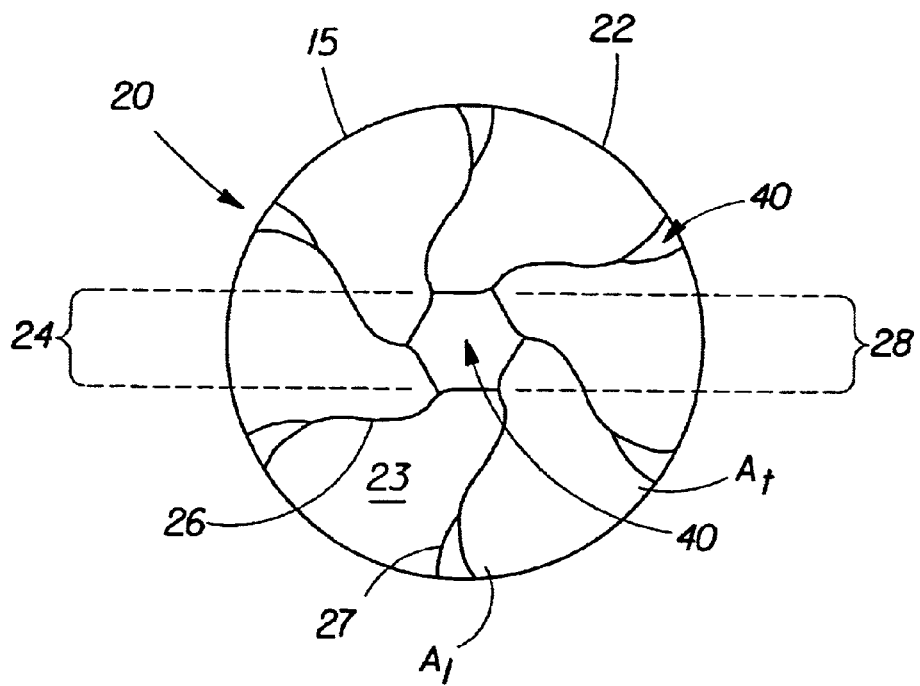
FIG. 1b shows a top view of the preferred applicator of FIG. 1a, having 6 curved petals and showing also a tip opening.

FIG. 1b shows a top view of an applicator 10 of the invention and it shows in more detail the insertion tip 20 of the applicator 10. The petals have a first edge 26 and a second edge 27, extending from the edge 15, so that thus the petals 23 as a whole extend from the edge 15, to the top region 24 of the tip 20.

The first edge 26 and the second edge 27 converge (or optionally they are connected with a third edge) at the top region 24 or side of the insertion tip 20; preferably, there is an opening 28 in the top region of the insertion tip, through which the tampon is visible.

Two or more of the petals 23 typically have an area of overlap with the neighbouring petal. Preferably, each petal has an area of overlap with a neighbouring petal. The overlap is preferably obtained in a regular manner, e.g. each first edge 26, or part thereof, is positioned on top of a neighbouring second edge 27 of a neighbouring petal 23, or part thereof, or each first edge 26, or part thereof, is positioned under a neighbouring second edge 27 of a neighbouring petal 23. Thus, the overlap is preferably made in the same manner for each petal.

Figure 2A:
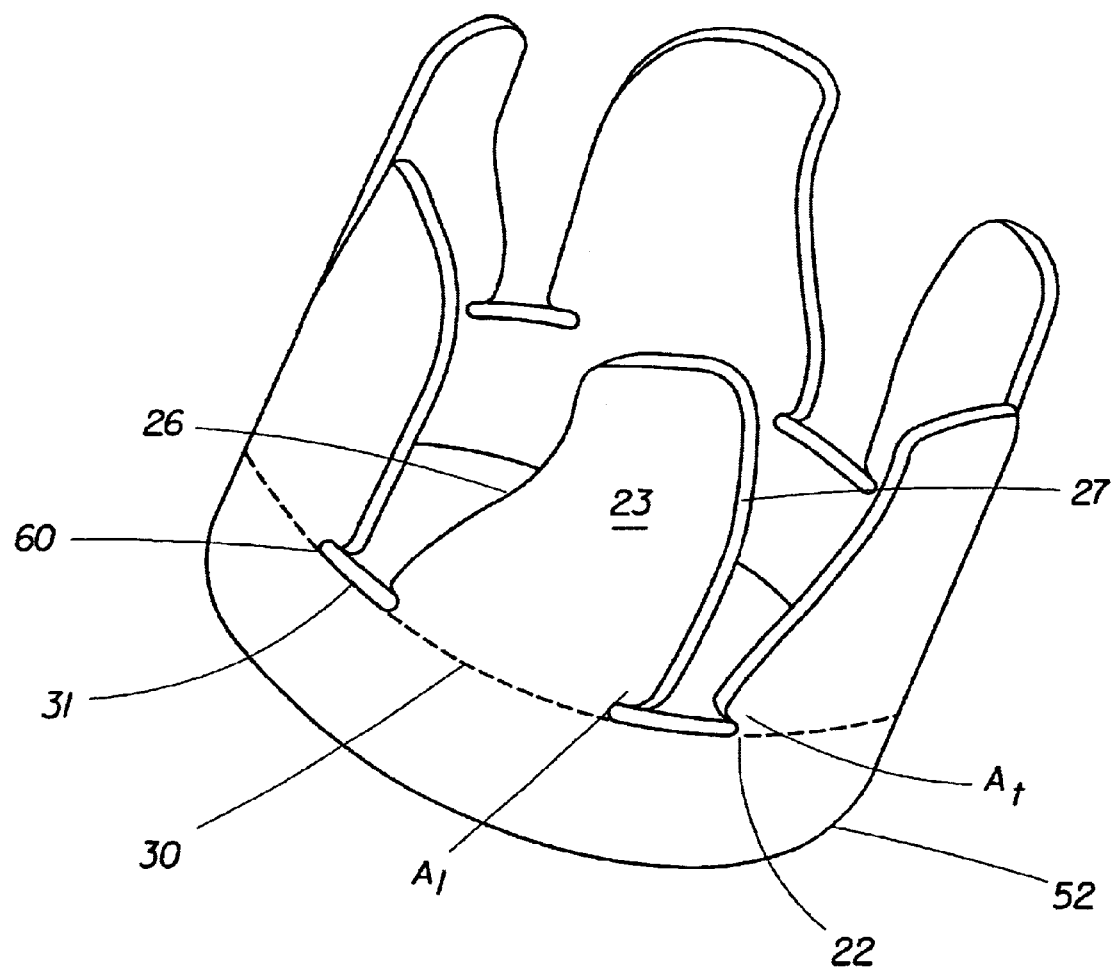
FIG. 2a shows a perspective view of part of an applicator unit whereby the 6 petals are opened.
Figure 2B:
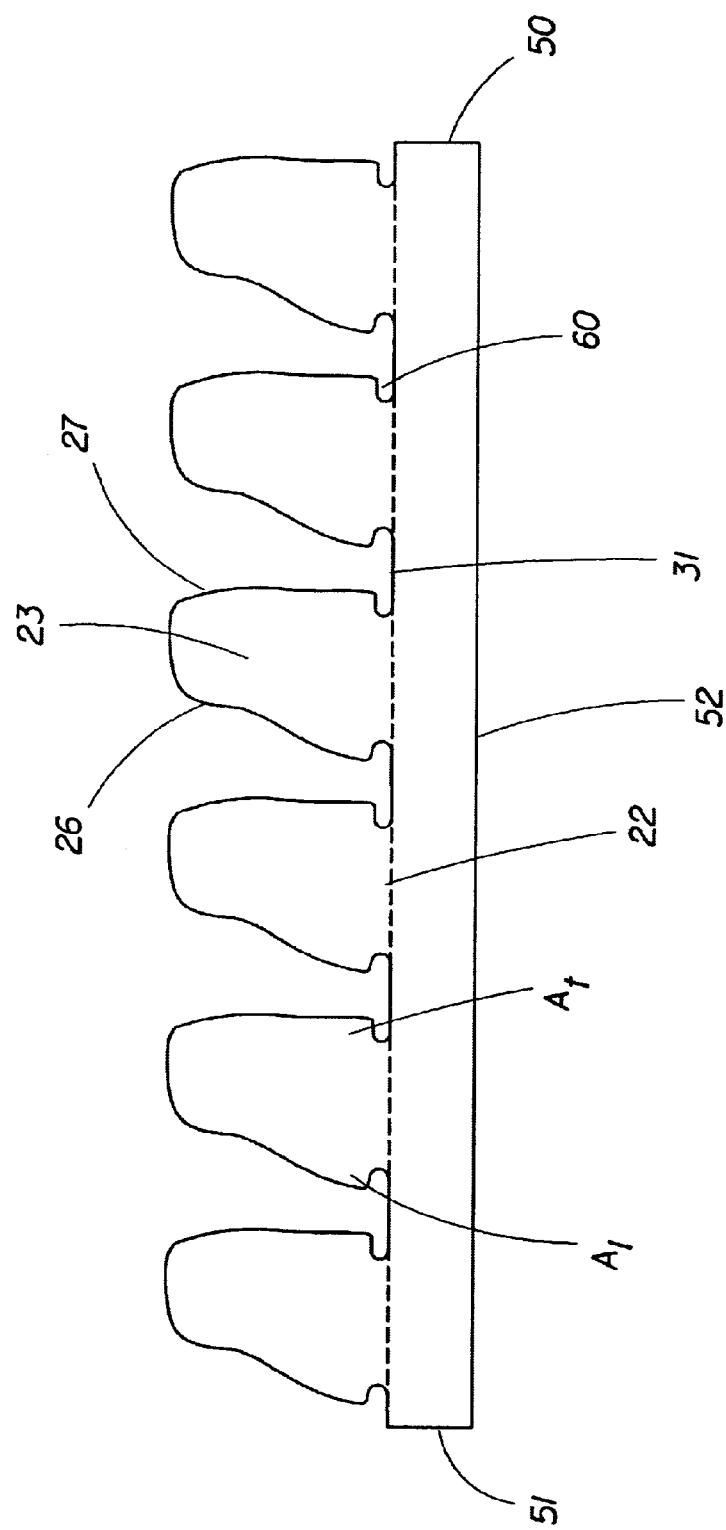
Figure 3:
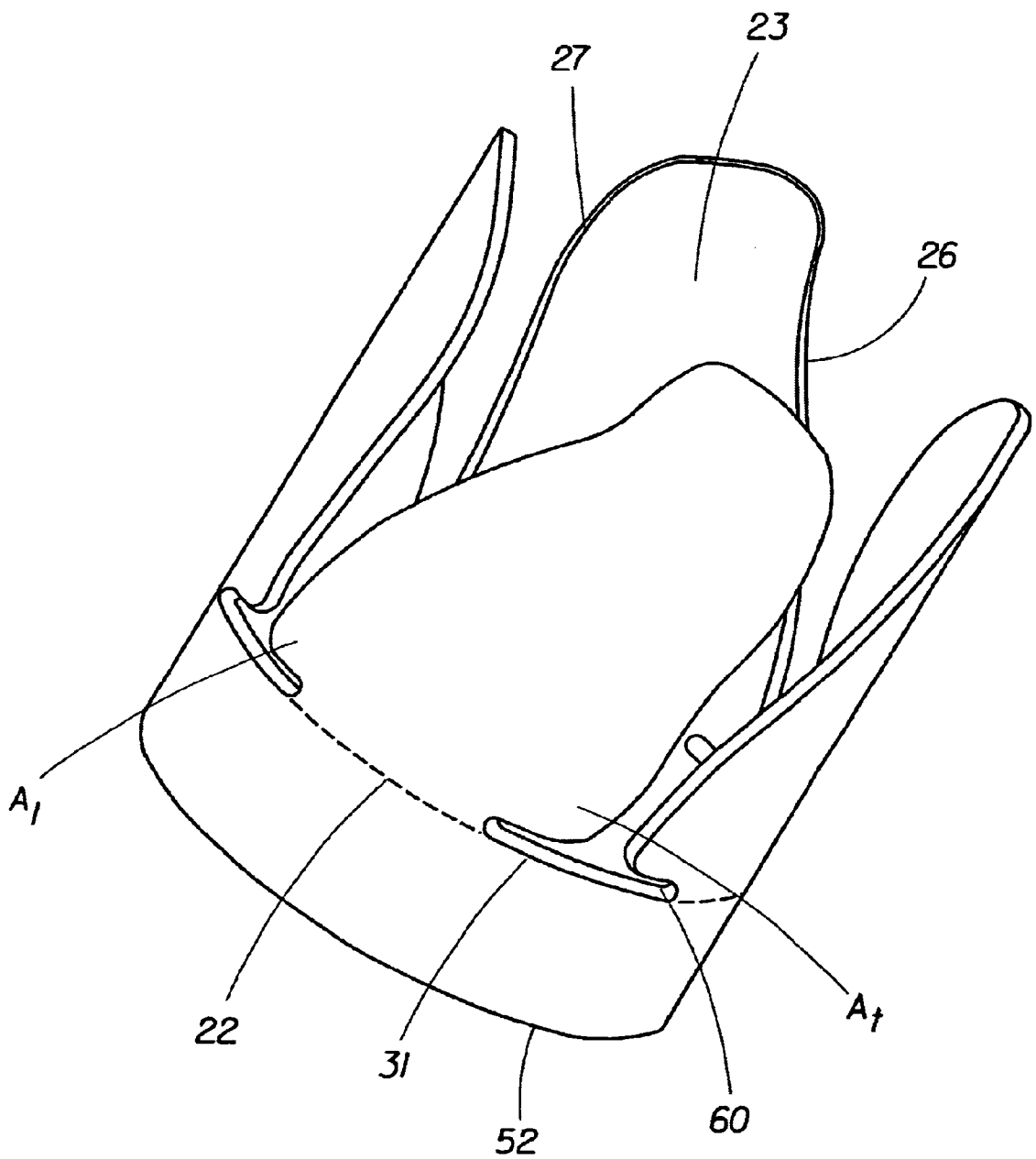
FIG. 3 shows a perspective view of part of an applicator unit whereby the 4 petals are opened.

The first edge and/or the second edge are preferably curved, so that the edges 26, 27 can converge at the top region 24 of the insertion tip; this may be in the shape of a sharp tip, but it is preferred if they converge in the more rounded tip, as can be seen in FIGS. 2a, 2b, and 3.

The petals 23 may have any width, length, thickness or shape, for example depending on the number of petals 23 present; preferably the length of the petal 23 from the bottom line 22 or lowest point (i.e. furthest removed from highest point of petal) of the petal 23 to the highest point of the petal, indicated in FIG. 1a as H, is from 5 to 20 mm, or even from 7 to about 15 mm or even to 12 mm.

The first edge 26 and/or the second edge 27 is preferably positioned with an angle with the edge 15 of the tube's 11 end portion or the bottom line 22 of the petal. Preferred is that one or more of the petal 23 (preferably all petals 23) have a first edge 26 with an angle $A_l$ with the edge 15 or bottom line 22 of between 20° and 80°, preferably 40° to 60°, and a second edge 27 with an angle $A_t$ with the edge 15 or bottom line 22 of 180°—$A_l$, or visa versa. It is clear from the figures that the angles, as used herein, are the internal angle of the petals.

Preferred is that the first edge 26 is the leading edge with an angle $A_l$ as specified above and that the second edge is the trailing edge with the angle $A_t$ as specified above. Preferred is that the leading edge 26 or part thereof of a first petal 23 is positioned on top of the trailing edge 27 of a directly neighbouring, second petal 23.

The insertion tip 20 has preferably a top region 24 with an opening 28. This opening 28 may be defined by one or both edges 26, 27 of the petals 23, or if the edges do not converge, the opening 28 may be defined by one or both edges 26, 27 and a connecting edge. The opening 28 may have any shape, but in preferred executions the shape is substantially triangular (in particular when 3 petals are present) or circular (when 5 or more petals are present). The opening 28 has a geometrical centre point and a shortest dimension through this geometrical centre point. This dimension is preferably less than 10 mm or even less than 5 mm.

An opening 28 which is substantially triangular has preferably a shortest dimension which is the height of the triangle of the values below and an opening which is substantially circular opening has preferably a shortest dimension which is the diameter, of the values below, and an otherwise shaped opening may have a shortest dimension through the geometrical centre point, as below, namely: preferably from 1.5 mm to 5.0 mm or even from 2.0 mm to 4.0 mm or even 2.75 mm to 3.25 mm. This is in particular preferred for an applicator 10 with 6, 7 or 8 petals or more, whilst the shortest dimension may be larger for an applicator 10 with 3, 4 or 5 petals 23, for example between 3.0 mm to 10.0 mm, or even 4.0 mm to 8.0 mm or even from 4.5 mm to 7.5 mm.

Preferably for an applicator 10 with 6 petals 23 or more is that the opening 28 is approximately circular, as is shown in FIG. 1b. The opening 28 may be defined only by the first edges 26 of the petals 23, or only by the second edges 27 of the petals; typically the opening 28 is at least defined only by the edges which lay on top of the other edges, e.g. in a preferred embodiment thus the leading edges. Preferred is that the opening 28 has a shortest dimension of less than 5 mm, preferably less than 4.5 mm, and/or preferably more than 1 mm, or even more than 2 mm, or even more than 2.5 mm, or even more than 3 mm.

As said above, it has been found that the presence of an opening 28 may be beneficial to reduce the expulsion force needed to expel a tampon 40 through the petals 23. The inventors found also a relationship between the force to open a petal 23 and the size of the shortest dimension. Thus, a too large an opening 28 may reduce the hygiene of the tampon 40, because more of the tampon 40 is exposed, and also, a too large an opening 28 may reduce the force to open an individual petal 23 too much, which makes it too easy to open a petal 23 with an external force, resulting in a higher risk that a petal 23 opens prior to use.

The inventors also found that another factor, which may influence the required force to open an individual petal, is the length of the petal 23 and/or the angles $A_t$ and $A_l$, described above.

Preferred is that the force to open a petal 23 is more than 50 g-force, preferably more than 90 g-force, or even more than 120 g-force or even more than 140 g-force, and preferably less than 600 g-force, or even less than 400 g-force, or even less than 250 g-force, as may be measured by the method described below.

Preferred is an applicator 10 which has a linear relationship between the shortest dimension L (in mm; for example height or diameter) and the force to open a petal (Fto), as determined by the method below. The linear relationship for the applicators 10 herein is typically always a negatively sloping linear relationship, which typically has a $R^2$ (as defined below) of at least 0.4.

For an applicator herein which has 6 petals as described herein with reference to FIGS. 1a, 1b and 2a, the linear relationship is preferably as follows: Fto (in g-force)=−40×L (in mm)+235, whereby the deviation as defined as $R^2$ is preferably at least 0.4.

$R^2$ is derived from the error or deviation between the Fto found by experiment (as described below) and the Fto found by use of the calculation above, for a given L, thus the error or deviation e:

$e = Fto\text{-experimental} - Fto\text{-calculated}$ $R^2$ is then the sum of squares of the series of error e for at least 3 data points which are identical except for the different L's, which involves the square of all of the e's for a data set added together:

$$R^2 = 1 - \frac{SSE}{SST}$$

where $$SSE = \sum (Y_i - Y_i)^2$$

and $$SST = \left(\sum Y_j^2\right) - \frac{\left(\sum Y_j\right)^2}{n}$$

This is also discussed in '*Probability and Statistics for Engineers and Scientists*', by Ronald E. Walpole and Raymond H. Myers, Third Edition, 1985: ISBN 0-02-424170-9. This can be calculated by Microsoft Excel, as also is explained din the Microsoft Excel help files.

The force to open a petal 23 (Fto) of an applicator 10 which has an opening 28 in the insertion tip can be determined as follows.

The applicator 10 is placed in a holder of a test device, such as a MTS machine, using a Testwork 4.0 programme, as to keep is fixed in that position. Thus, the insertion tip 20 extends from the holder in horizontal position. A vertically hanging crochet hook of 1.0 mm, which is not sharp, is placed in front of the insertion top 20, as to line up with the opening 28. The applicator 10 in the holder is then pushed towards the hook, such that the hook is positioned in the opening 28, under one single petal 23. Then, the hook is raised and it lifts thereby said petal 23 upwards. The force applied on the hook is measured by the device. If the petal 23 slips off the hook, the test is stopped. The force to open a petal 23, Fto, is the highest force registered during the experiment, from the moment the hook starts lifting the petal 23 up to the moment the petal 23 slides off the hook.

If the insertion tip with the petals does not have an opening, an opening can be made (by for example opening one or more of the petals slightly) which is just large enough to be able to insert the hook in the experiment above.

For example, preferred applicators 10 have an opening with a shortest dimension L of 2.1 mm to 4.5 mm and an Fto of 150 to 75 g-force, or more preferably a L of 2.5 mm to 3.8 mm and a Fto of 130 to 95 g-force. A preferred angle $A_l$ of the latter may be from 45 to 55°.

The applicator is preferably such that it has a low maximum expulsion force, namely preferably of less than 1000 g-force, or even less than 600 g-force, or even less than 600 g-force or even less than 400 g-force or even less than 325 gram force, and in highly preferred executions this may be even lower, for example less than 300 g-force, or even less than 250 g-force. Preferred may also be that the applicator has a minimum expulsion force of at least 50 g-force, or even 75 g-force.

When used herein, the maximum expulsion force is the highest force observed during full intended expulsion of the tampon 40, measured independent of the body (e.g. out side the human body). Therefore, the maximum expulsion force combines all force aspects of the applicator 10, including the force to open the petals 23. The maximum expulsion force will measure not only the force needed to open the petals 23 to expel the tampon 40 past the petals 23, but includes other factors such as friction between the tampon and applicator unit.

The maximum expulsion force can for example be calculated as follows:

An applicator 10 as shown in FIG. 1a is obtained. The tampon 40 of the applicator 10 is submitted to a force, namely onto the tampon bottom side, to expel the tampon 40 from the applicator 10, thereby applying a force on the inside of the petals 23 and opening the petals and then travelling passed the petals 23, out of the applicator.

This can be done by use of a Dillon Force Gauge (Mecmesin AFG50N). The measurement is done by following the operator manual on how to measure the peak expulsion force.

The force gauge is oriented such that the load cell 'foot' will travel in the horizontal direction, and it is mounted to a stand and it remains stationary during the test. Also affixed to the stand to one side of the force gauge is a propellable moveable horizontal slider, controlled by a linear actuator. Attached to the slider is an anchored applicator clamp to hold the applicator 10 or the tube 11 thereof stationary during the test, but without deformation of the applicator 10. The internal diameter of the clamp is set corresponding the diameter of the applicator, typically between 12–18 mm.

So when using a telescoping tubes applicator 10, when the inserter tube 11 with the insertion tip 20 with petals 23 is anchored to the slider by the applicator clamp, the push tube 14 is still free to slide within the inserter tube 11.

The slider and force gauge are so aligned on the stand that the push tube's longitudinal axis and the force gauge's load cell axis are in-line with each other, in this case a horizontal line. The non-expulsion end of the push tube 14 and the load cell 'foot' are positioned to face each other.

When the slider is attached, it will move the applicator 10 towards the load cell foot. The measurement is done with the slowest, constant speed setting of the device; a speed of 9 cm/sec is an exemplary speed for the test of the applicator 10 of the invention. When the slider engages the end of the push tube 14 against the load cell foot, the push tube starts its travel within the inserter tube 11, first engaging the bottom of the tampon 40 and then expelling the tampon through petals 23. All the while, the force gauge measures the expulsion force, as well as captures the peak expulsion force. The slider stops its movement towards the force gauge after expelling the tampon 40 from the applicator 10 by the operator manually turning off the slider power source (engaging a switch or using some other form of control which can cut the power). To one skilled in the art, other fixtures can be constructed using any reliable peak force measurement gauge to measure the expulsion force at a given speed, which is herein referred to as maximum expulsion force.

Preferably both edges 26, 27 are curved, and preferably in such a manner that they still converge at the top region 24, without the need of a connecting edge having an angle with both the first edge 26 and second edge 27. This can also bee seen in more detail in FIG. 3.

Each petal 23 preferably has an area of overlap with a neighbouring petal 23, such that each petal 23 lies on top of one directly neighbouring petal 23, to have an area of overlap with that petal 23 and under another directly neighbouring petal 23, to form another area of overlap.

The exact percentage of overlap of course depends on the size and shape of the petals. In a preferred execution the petals are of equal size and shape and the areas of overlap area all equal in size and shape. Typically, the higher the number of petals 23 is, the higher the percentage of overlap.

The first petal 23 laying on top of a second petal 23 has preferably an area of overlap with that petal 23 of at least 0.5%, or even at least 1% or even at least 3% or even at least 4% of the surface area of said second petal 23, and in certain preferred executions, the area of overlap may even be more than 5% or even more than 7% or even more than 10%, but typically in about all embodiments preferably less than 50% or even less than 35% or even less than 30% or even less than 20% of the surface area of said second petal 23

FIG. 2a shows a perspective view of part of the applicator 10, namely the insertion tip 20, with 6 petals 23. The petals 23 are in opened position; this position is typically achieved after the tampon has travelled through the petals, into the body.

The petal 23 has a first edge 26 and a second edge 27 which are both curved and which converge at about the highest point of the petal.

The angle $A_l$ and $A_r$ are the angles between the edges 26, 27 and the bottom line 22 of the tampon petals, and these angles are preferably as described above. The bottom edge 52 of the insertion tip 20 will be connected to the top portion of the applicator tube 11 and connecting line will form the edge 15 of the applicator tube 11, as described above.

The petals are preferably not connected to one another, except by the area of the insertion tip 20 below the bottom line 22, which is through the (imaginary) bottom edges of the petal downwards. It is even preferred that the petals 23 have bottom portions 30 which comprise the bottom edge's line 22, which are spaced apart, e.g. that there is one or more gaps 31 between the bottom portions 30 or edges 22 of the petals 23.

FIG. 2b shows a part of a series of insertion tip units (i.e. about one unit), prior to formation into an insertion tip 20 as shown in FIG. 2a. Thus, such a unit may be used to make the applicator's tip 20 of the invention, which can then subsequently be connected to an applicator tube 11. Then the insertion tip's edges 50 and 51 are simply moved together and fixed, to typically form a cylindrical ring of petals, which can then be connected to a cylindrical tube 11, typically of about the same diameter as the ring of the insertion tip 20. Typically this is done by connecting part of all of the area between the bottom line 22 and the insertion tip unit's edge 52 to a tube 11.

The series of insertion tip units as shown in FIG. 2b, can also be much longer, comprising a multitude of such units. Then this multitude of units can simply be cut in the units as shown in FIG. 2b and subsequently be shaped in to the applicator.

Of course, the series of petals 23 as shown in FIG. 2b may also be integral with the material, which is to form the tube 11, so that an applicator 10 is obtained, whereby the tube 11 and the insertion tip 20 are integral with one another.

Just as FIG. 2a, FIG. 3 shows a part of an applicator 10 with the petals 23 opened, the difference being that FIG. 3a shows a part of an applicator with 4 petals, rather than the 6 petals of FIG. 2a and 2b.

Figure 4A:
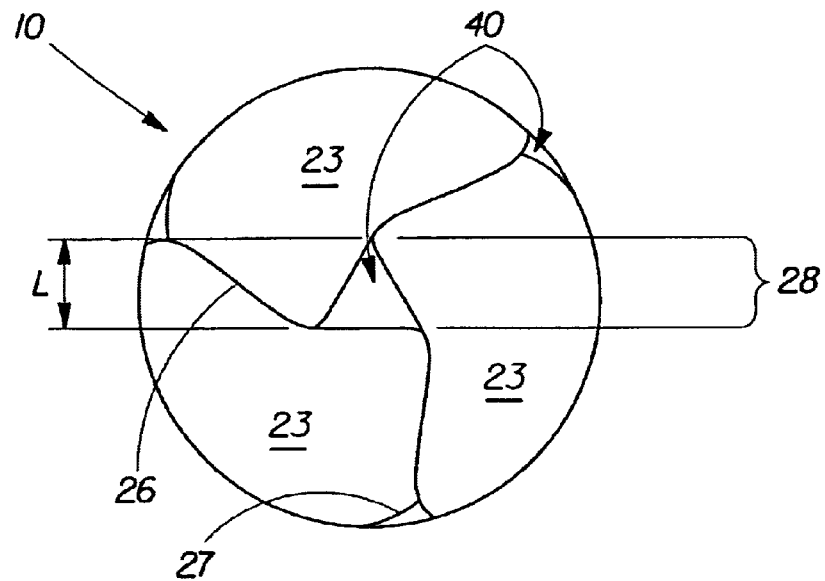
FIG. 4a shows a top view of a preferred applicator of the invention having 3 curved, overlapping petals.

FIG. 4a shows a top view of a top portion of an insertion top 20 of an applicator 10 of the invention having 3 petals 23, which overlap such that each petal 23 is partially on top of one neighbouring petal 23 and partially under the other neighbouring petal 23.

Figure 4B:
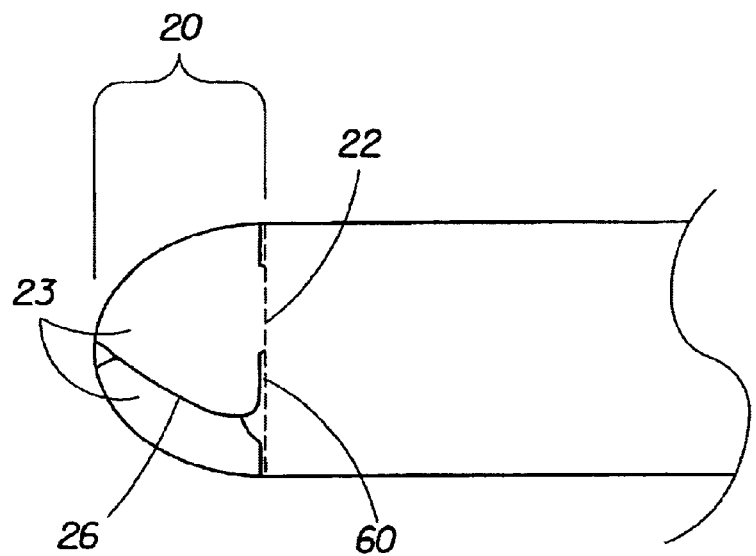
FIG. 4b shows a side view of the preferred applicator of FIG. 4a, having 3 curved, overlapping petals.

In FIG. 4b it can be seen how the petals 23 are overlapping, but that they are not attached to one another beyond the bottom line 22 of the petals 23. The preferred petals 23 are curved and to achieve this, they are not only cut in the specific shapes as shown in FIG. 2a and 3, but they are also twisted. Thereto, the petals 23 are preferably cut with one or more side cuts 60, which allow twisting of the petals 23 to a certain extent. This can furthermore be seen in FIGS. 2a, 2b and 3.

As can be seen in FIG. 4b, but also in FIG. 1a, the insertion top 20 is preferably rounded or dome-shaped, in particular when 3 or 6 or more petals are present. When 4 petals or possibly when 5 petals are present, the insertion tip may be more pointy shaped or oval-shaped.

Process for Making the Applicator

The applicator can be made by any process known in the art, involving as modification to the known processes, a step of cutting the petals in the required size and shape, for example, curved such that the petals have no sharp, pointy top, i.e. such that the edges of a petal do not converge in the highest point, but elsewhere, as can be seen in FIG. 2a. Typically, the process also involves a step of shaping the insertion tip, typically after cutting the petal shapes, such that the petals overlap with one another and conform to the shape of the mould used in the process (as described below) or for example the tampon top portion, e.g. radially curved to form a dome-shape.

A preferred process for producing the applicator with the tampon of the invention involves the step of first obtaining an applicator tube portion, typically a cylindrical open ended tube, and typically of winded material, and subsequently cutting a series of open-folded (e.g. in one plane) insertion tip units, or a single insertion tip unit, and cutting therein, the required amount of petals, of the desired shape and size. Such an open-folded, insertion tip unit(s) with cut-out petals can be seen in FIG. 2b. The insertion tip unit(s) obtained may be in one plane, and the unit(s) still need to be shaped to fit the applicator tube (e.g. made cylindrical) and to let the petals converge at the top of the insertion tip. If a series of units is obtained, this series of units may then be cut into individual units.

However, it may be possible to make the insertion tip of a piece of material which is already in the shape of the tube, e.g. a cylindrical open ended piece of material or second tube, and to cut the petals out of this material.

The cutting step can be done my any method known in the art, and it may involve a number of individual cutting steps.

To shape the insertion tip unit into an insertion tip, used for the applicator, the unit may preferably be placed in or over/around a mould, which has the shape, which the insertion tip ultimately needs to acquire, i.e. the shape of the top portion of a tampon. The mould may be a tampon, or the applicator tube with the tampon, or it may be a separate device such as a mandrel.

If the mould includes the insertion tube and tampon, the petals shaping step and closing step and the step to attach the insertion tip to the tube may all be done while the insertion tip is placed over the tampon. Then the mould is typically the tampon top portion and the petals conform to the shape of the tampon top portion.

If a separate mould is used, such as a mandrel, then the petals are preferably first partially shaped or preformed, as described below, and then the tampon is inserted through and past the petals and the petals are (twisted and) closed, or the petals are first shaped as described below and the tampon is inserted in the tube form the opposite end to the petal end.

Typically the folding step involves that the open folded unit is first shaped to fit the applicator tube, e.g. by connecting the edges of the insertion tip unit so that the required cylindrical shape is obtained. This may be done by use of the mandrel as well.

Then, the unit is for example placed in, over or around a tampon-head-shaped mould, for example around a mandrel and the petals are shaped such that they obtain the required curvature, e.g. the same curvature as the tampon top portion, which is to be used in the final applicator.

However, if the mould is not an applicator tube with a tampon, then it may be preferred that the petals are not yet 'permanently' radially curved towards each other to form a closed insertion tip, but it may be preferred that they are only curved to the required shape and then left open in this shape, until the tampon is inserted in the applicator, through and past the curved but still open petals.

The shaping may for example be done by contacting the insertion tip units or the petals thereof with a heat and/or pressure source, for example by contacting the insertion tip unit on the mandrel with a heated surface and putting pressure on this surface.

Typically the insertion tip unit with shaped petals is then attached to the insertion tube and the tampon is inserted into this arrangement (if not already integral therewith).

Then, in a closing step, the petals are closed by folding the petals again into the shape given to them by the mould, as describe above. Typically, the design of the insertion tip and the closing step are such that a small opening is obtained at the top of the insertion tip If the tampon is already present in the insertion tube, the closure step may be done at the same time as the shaping step, using the mould.

Preferred is that, prior to or simultaneous with the closing step, the petals are twisted, to obtain the required overlap. This may for example be done by a device which grabs the top of each petal individually and twist this in the required direction.

The insertion tip can be connected to the tube by any method and at any stage of the applicator making process. Preferred may be that the insertion tip unit is attached to the tube, after the petals are cut, but prior to the petal shaping step.

Of course, the applicator tube and the insertion tip may be unitary, in which case the connecting step is not needed. Then the same process as above can be used for shaping the tube-tip unity. For example, a unitary tube-tip unity can be placed in, over or around a mould, for example a mandrel or tampon, and edges of the open tube-tip unit may than be attached so that it obtains an open ended, cylindrical form of the mandrel or tampon, and then the petals may be shaped as describe above, and optionally the tampon is still inserted.

Of course the applicator may also comprise more than one tube. The second tube is then typically present inside the first tube, to which the insertion tip is connected or with which it forms a unity. The second tube may be inserted at any stage, preferably at the tame time or directly subsequent to insertion the tampon is inserted in the first tube.

Preferred is that the process is a continuous process, as used to make applicators known in the art. It may be preferred for process efficiency that the applicator construction is done as a separate process (e.g. off-line), to the process of inserting the tampon and/or second tube, because the former may be a slower process and performing all steps, including the slowest in one continuous process would then the reduce the overall speed and efficiency.

What is claimed is:

1. An applicator capable of receiving a tampon, having a tube with a first end portion and a second end portion, the first end portion having an end portion edge, which is connected to or integral with a dome shaped insertion tip, said insertion tip extending from said end portion edge and having at least 3 petals;
    each petal having a first edge and a second edge, wherein the first edge and the second edge of each petal extends from said end portion edge;
    wherein for each petal, at least a portion of the first edge of the petal is posititioned on top of at least a portion of one directly neighbouring petal and at least a portion of the second edge of said petal is positioned under another directly neighbouring petal to form, for each petal, a region of overlap; and
    wherein said tampon is expelled through said petals of said applicatior.

2. An applicator as in claim 1 wherein the first edge is a leading edge which has an angle $A_l$ of between 20° and about 80° with said end portion edge, and the second edge is a trailing edge which as the angle $A_t$ of 180°-$A_l$, with said end portion edge.

3. An applicator as in claim 1 wherein the second edge is a leading edge which has an angle $A_l$ of between 40° and about 60° with said end portion edge, and the second edge is a trailing edge which has an angle $A_t$ of 180°-$A_l$, with said end portion edge.

4. An applicator as in claim 1, comprising a tampon, wherein the expulsion force to expel the tampon from the applicator is less than about 500 g-force; and
    wherein the force to open a single petal is more than about 75 g-force.

5. An applicator as in claim 1, comprising a tampon, wherein the expulsion force to expel the tampon from the applicator is less than about 325 g-force; and
    wherein the force to open a single petal is more than about 90 g-force.

6. An applicator as in claim 1 wherein the overlap between a first petal and a directly neighboring second petal is at least about 3% of the surface area of the second petal.

7. An applicator as in claim 1 wherein the overlap between a first petal and a directly neighboring second petal is at least about 10% of the surface area of the second petal.

8. An applicator as in claim 1 having from about 3 to about 6 petals.

9. An applicator as in claim 1 having from about 3 to about 4 petals.

10. An applicator as in claim 1 wherein the first edge and the second edge of a petal are curved.

11. An applicator as in claim 1 further comprising a tampon.

12. An applicator capable of receiving a tampon, having a first end portion and a second end portion, the first end portion having an end portion edge, which is connected to or integral with an insertion tip said insertion tip extending from said end portion edge and having at least 2 petals;

- each petal having a first edge and a second edge, extending from said end portion edge, wherein the first edge and the second edge converge at a top region of the insertion tip and whereby there is an opening in the top region of the insertion tip;
- wherein the force to open a petal is at least about 50 grams; and
- the opening has a shortest dimension through a geometrical centre point of the opening of less than about 10 mm; and
- wherein for each petal, the first edge is positioned on top of one directly neighbouring petal and the second edge is positioned under a second directly neighbouring petal to form, for each petal, a region of overlap.

13. A process for making an applicator suitable to comprise a tampon comprising the steps of:

A) cutting at least 2 petals into a hollow tube;

B) shaping the petals in or over a mould which at least partially has the shape of the tampon to be comprised by the applicator, to obtain a hollow tube with petals which conform to the shape of the mould;

C) twisting the petals; and

D) closing the petals.

14. A process for making an applicator suitable to comprise a tampon comprising the steps of:

A) cutting at least 2 petals into material suitable to form a hollow tube;

B) shaping the material into a hollow tube;

C) shaping the petals in or over a mould which at least partially has the shape of the tampon to be comprised by the applicator, to obtain a hollow tube with petals which conform to the shape of the mould;

C) twisting the petals; and

D) closing the petals.

* * * * *